United States Patent [19]

Dodgson

[11] 4,052,990
[45] Oct. 11, 1977

[54] MEDICO-SURGICAL TUBE AND ADAPTOR

[75] Inventor: Roy Howard Dodgson, Hythe, England

[73] Assignee: Smiths Industries Limited, London, England

[21] Appl. No.: 598,315

[22] Filed: July 23, 1975

Related U.S. Application Data

[63] Continuation of Ser. No. 461,202, April 15, 1974, abandoned.

[30] Foreign Application Priority Data

Apr. 16, 1973 United Kingdom ............... 18193/73

[51] Int. Cl.² .................. A61M 25/00; F16L 55/00
[52] U.S. Cl. ................... 128/351; 128/208;
128/247; 285/177; 285/260; 285/331;
285/334.3; 285/423
[58] Field of Search ............. 285/260, 242, 235, 331,
285/334.3, 423, 424, 177, 239; 128/214.2, 221,
247, 334 C, 334 R, 351, 277, 350 R, 349 R, 208;
138/89

[56] References Cited

U.S. PATENT DOCUMENTS

| 2,638,096 | 5/1953 | Waldhaus | 128/208 X |
| 3,361,306 | 1/1968 | Grim | 128/208 UX |
| 3,484,121 | 12/1969 | Quinton | 285/242 |
| 3,745,999 | 7/1973 | Deaton | 128/277 |
| 3,874,377 | 4/1975 | Davidson | 128/351 X |
| 3,880,452 | 4/1975 | Fields | 285/423 X |

FOREIGN PATENT DOCUMENTS

| 1,216,808 | 11/1959 | France | 285/239 |
| 1,801,568 | 5/1970 | Germany | 285/239 |
| 74,732 | 12/1947 | Norway | 285/239 |
| 10,423 | 5/1895 | United Kingdom | 285/239 |
| 196,255 | 8/1967 | U.S.S.R. | 128/351 |

Primary Examiner—Werner H. Schroeder
Assistant Examiner—Moshe I. Cohen
Attorney, Agent, or Firm—Pollock, VandeSande & Priddy

[57] ABSTRACT

A tubing adaptor of unitary plastics construction is assembled with an endotracheal or other medico-surgical tube for coupling the tube to a connector or tubing of larger diameter in a gas circuit. The adaptor has a tubular stem which closely fits into the tube and which extends from, and opens through, the base of the cup-shape body portion. The cup-shape body portion is for insertion in the passageway of larger diameter to establish the coupling, and the tubular stem is turned back on itself at its open end remote from the base so as to provide an external circumferential claw or lip that is splayed outwardly away from the open end so as to engage with the inside of the tube to restrain withdrawal of the stem from the tube. The claw may be formed by a step which involves the application of force uniformly around the whole circumference of the open end of the stem after that end has been splayed outwardly, against an inclined circumferential shoulder of a spigot. A die coaxial with the spigot is then moved along the spigot into abutment with the portion splayed out on the shoulder to urge this portion back on itself such as to leave the end turned back when the force is removed.

1 Claim, 8 Drawing Figures

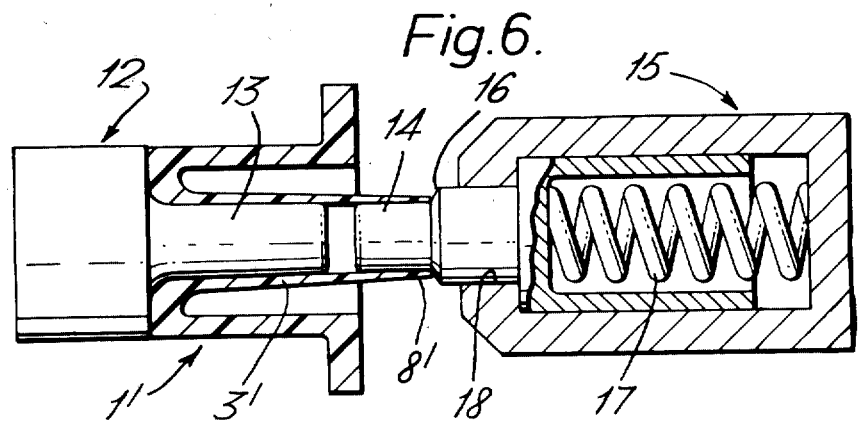
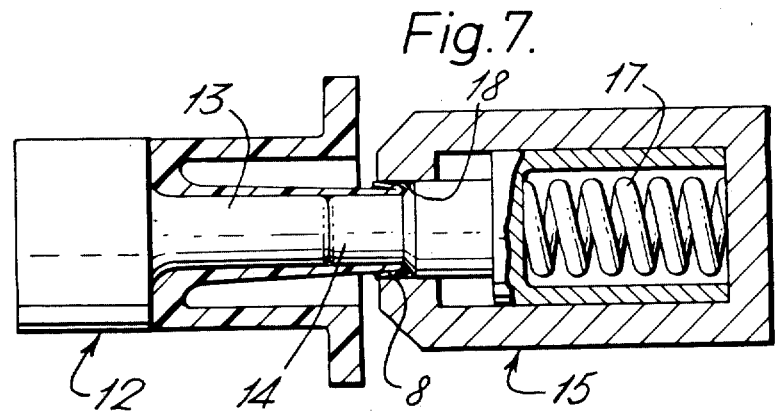
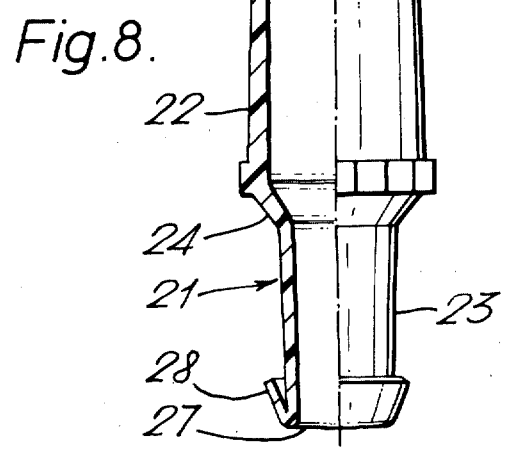

MEDICO-SURGICAL TUBE AND ADAPTOR

This is a continuation of application Ser. No. 461,202, filed Apr. 15, 1974, now abandoned.

This invention relates to devices for coupling to tubing.

The invention is concerned especially with devices for coupling to tubing, of the kind in which an open-ended tubular part of the device is for close-fitting insertion, and retention, within the tubing.

Devices of the kind specified in the preceding paragraph (referred to hereinafter as of "the kind specified") are used for example in surgical and medical applications, and especially for establishing connection to endotracheal tubes. Endotracheal tubes are commonly fabricated of polyvinyl chloride or similar plastics material and, where the device is fitted at the time of intubation or a short while before, such material normally provides sufficient resilience to maintain an adequate fluid- and mechanically-tight coupling throughout such use. However, there are applications for which the device is required to be coupled to the endotracheal tube well in advance of use, and for example, before packaging and sterilization of the tube. In these circumstances the natural relaxation of the plastics material of the tube that takes place progressively with time, may well become significant to the extent of prejudicing the continued maintenance of the necessary fluid- and mechanically-tight coupling. Thus there is the danger that the integrity of the coupling will have become seriously impaired when the endotracheal tube with the fitted device, is eventually taken into use. It is one of the objects of the present invention to reduce this danger.

According to one aspect of the present invention there is provided a device of the kind specified wherein the tubular part turns back on itself at its open end to provide an external claw for engaging with the inside of the tubing and thereby resist withdrawal of the said part from within the tubing.

The claw may extend, as a circumferential lip, completely around the said open end.

The device of the invention may be simply an end fitting for terminating the tubing, but it may be a device (for example a valve) having a function beyond this. Furthermore, the device may be entirely, or only partially, of a tubular configuration, and in the former case may in fact be tubing having the said claw formed at one end; in such a case it is possible to achieve a direct coupling between two lengths of tubing by inserting one within the other for retention with one another by the action of the claw.

Although the invention is not limited to application in the medical and surgical field, it is of especial advantage in connection with the problem of relaxation with time of plastics material used in this field. More specifically in this respect, and as indicated in general terms above, it is common practice to supply certain forms of endotracheal tube already fitted with an adaptor device that is for use in coupling the intubated tubing into the gas circuit by which air and other gases are administered to, and ventilated from, the patient's lungs during anaesthesia.

The tubes and connectors used externally of the patient in anaesthesia are generally provided to comply with an internationally-agreed standard that is based on a normal passageway-diameter of 15 millimeters. The lumen diameter of an endotracheal tube, however, is normally significantly less than this, and the adaptor serves to effect the necessary gas-tight transition in diameter between the endotracheal tube and the rest of the gas circuit. In this respect the adaptor has an open-ended tubular stem which is for close-fitting insertion into the endotracheal tube, and which extends from and opens through the base of a cup-shape body portion of the adaptor that is for close-fitting insertion into the tubing or connector having the larger internal diameter. The possibility of undesired withdrawal of the stem of the adaptor of this kind from the endotracheal tube, arising for example from progressive relaxation of the tube on the stem and prejudicial to the integrity of the coupling provided, may be considerably reduced in accordance with a feature of the present invention, by the provision of a claw at the open end of the stem for engaging with the inside of the endotracheal tube. More especially the stem may turn back on itself around the whole of its open end so as to provide the claw circumferentially of that end.

Tubing adaptors used with endotracheal tubes are conventionally provided as mouldings of a plastics (for example, polypropylene, nylon or acetal-copolymer) material, and whereas it is in general possible to use a moulding process for the direct formation of a device having the claw feature of the present invention, this may necessitate the use of a longitudinally-split mould or present other difficulties and disadvantages. Difficulties and disadvantages of this nature, arising where the tubular-end part of the device is of a resilient plastics material (for example polypropylene or nylon, or possibly acetal copolymer material), may be overcome in accordance with another aspect of the present invention. According to this latter aspect, the present invention provides a method of tubular-end forming of a member of resilient plastics material, wherein force is applied to an open-ended tubular portion of said member to turn it back on itself around that end and leaving it turned back when the applied force is removed.

The method of the present invention specified in the immediately preceding paragraph is applicable to the formation of the claw feature on a tubing adaptor or other device referred to above, and the application of the method in this respect may be as an operation that follows on from a plastics moulding process in the manufacture of the completed device. Furthermore, the force used in the method, which may be applied susbstantially uniformly around the whole circumference of the open-ended tubular portion, may be applied to the end of the tubular portion after that end has been splayed outwardly against, for example, an inclined shoulder of a tool.

An adaptor for fitting to an endotracheal tube, and a method of manufacture thereof, both in accordance with the present invention, will now be described by way of example, with reference to the accompanying drawings, in which:

FIGS 6 and 7 are sectional side elevations illustrative of successive stages of manufacture of the adaptor of FIGS. 1 to 3 from the moulding of FIG. 5; and FIG. 8 is a part-sectional side elevation of an alternative form of the tubing adaptor.

Figure 1:
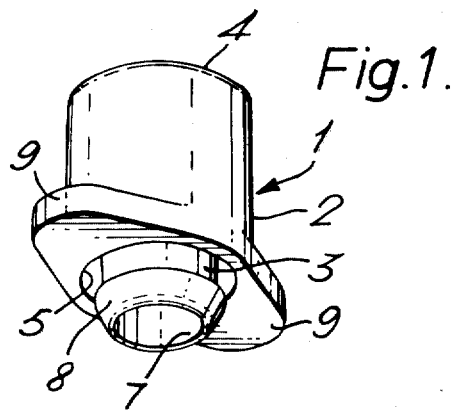
FIGS. 1 to 3 are a perspective view, a sectional side elevation, and a plan view, respectively, of the tubing adaptor.
Figure 2:
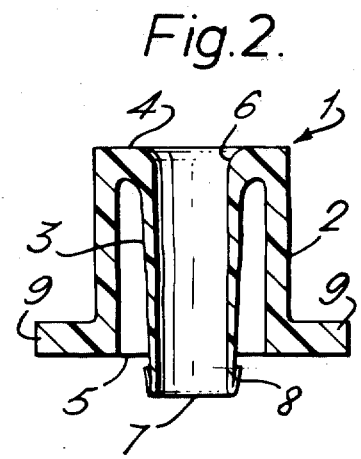
Figure 3:
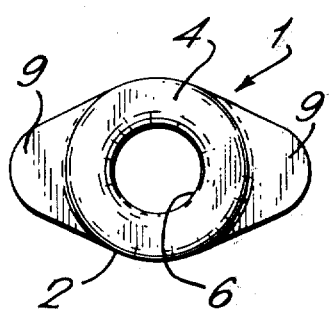

Referring to FIGS. 1 to 3, the adaptor 1 in this case is a unitary moulding of polypropylene having a cup-shape body portion 2 with an internal tubular-stem 3 that extends from the base 4 of the body portion 2 to project slightly from the open end 5 of the cup. The substantially-cylindrical external surface of the body portion 2 has a diameter-taper of 1 in 40 down towards the base 4 with a diameter of 15.47 millimeters at a distance of 10 millimeters from that end. The tubular stem 3, which is coaxial with the body portion 2 and opens through the base 4 with an outward conical flaring 6, is also tapered externally, but at a larger angle and down towards its open, free end 7. Around its open end 7 the stem 3 is turned back on itself to provide an external and circumferential lip or claw 8 splayed outwardly to increase in external diameter progressively back from the open end 7.

Figure 4:
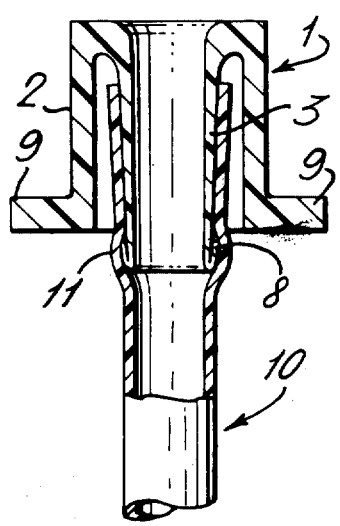
FIG. 4 is a sectional side elevation of an assembly comprising the adaptor of FIGS. 1 to 3 as fitted to the endotracheal tube.

Two diametrically-opposed flange ears 9 extend outwardly from the open end 5 of the cup to provide grips for the fingers during use. In this respect, and as illustrated in FIG. 4, the adaptor 1 is fitted in use to an endotracheal tube 10, with the stem 3 inserted in close fit within the proximal end of the tube 10. The adaptor 1 is coupled to the tube 10 in this way before packaging and sterilization, so that the tube 10 can be put to immediate use from the package without the necessity for any delay before intubation. Once intubation has been accomplished the tube 10 is coupled in the external gas circuit by standard hose directly, or through the intermediary of a standard connector, that is pushed onto the body portion 2 while the adaptor 1 is held at the finger-grip ears 9.

The tube 10, being of polyvinyl chloride, stretches readily to conform to the external surface of the stem 3 during the initial fitting of the adaptor 1. More particularly, the tube 10 bears up into a circumferential ridge 11 where it hugs tightly over the claw 8 of the stem 3, so that a good gas- and mechanically-tight coupling with the adaptor 1 results from the natural resilience of the tubing material. The integrity of this coupling is maintained irrespective of progressive relaxation of the material of the tube 10 that may in normal circumstances take place throughout the period (perhaps of months) before the endotracheal tube 10 is put into service.

Maintenance of the gas- and mechanically-tight coupling between the tube 10 and the adaptor 1, is facilitated by the inherent resilience of the claw 8 acting outwardly to maintain positive contact with the inner surface of the tube 10 within the ridge 11. Furthermore, any tendancy for the stem 3 to be withdrawn from the tube 10, or for the tube 10 to be pulled off the stem 3, is resisted by opening up of the claw 8 to dig or bite hard into the tubing inner-surface, and by tightening of the tube 10 over the claw 8 at the ridge 11.

Figure 5:
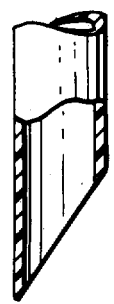
FIG. 5 is a sectional side elevation of a moulding from which the adaptor of FIGS. 1 to 3 is manufactured.

The adaptor 1 is manufactured from a moulding 1' which, as shown in FIG. 5, has the configuration of the adaptor 1 except at the free end of its central stem 3'. The stem 3' is moulded with an additional portion 8' projecting well beyond the open end 5' of the cup, and it is from this portion that the claw 8 is formed. More particularly, the additional stem-portion 8' is turned back into the claw 8 using tooling as illustrated in FIGS. 6 and 7.

Referring to FIG. 6, the moulding 1' is placed base first on a mandrel 12 with a spigot 13 of the mandrel 12 extending partway along the stem 3'. The spring-loaded spigot 14 of a claw-forming die 15 is inserted into the opposite end of the stem 3', and the die 15 is then urged forwards to bring the spigot 14 into contact with the spigot 13. By this operating the portion 8' of the stem 3' is splayed out circumferentially against an inclined circumferential shoulder 16 of the spigot 14. Further force applied to the die 15 overcomes the spring 17 acting on the spigot 14. The die 15 mounted coaxially with the spigot 14, is therefore moved axially of the spigot 14 into abutment with the splayed portion 8' and, as illustrated in FIG. 7, the consequent entry of the splayed portion 8' into the circular mouth 18 of the die 15, folds the portion 8' back on the rest of the stem 3' so as thereby to form the claw 8.

The adaptor described above with reference to FIGS. 1 to 3 is in accordance with the invention forming the subject of Wilmott et al co-pending U.S. Pat. application No. 449,316, filed Mar. 8, 1974, for "Tubing Adaptors", now abandoned, and U.S. Design application Ser. No. 398,057 filed Sept. 17, 1973, for "Tubing Adaptor Primarily for Medical Surgical and Veterinary Use", and assigned to the assignee of the instant application now U.S. Pat. No. Des. 237,552 issued Nov. 4, 1975. However the present invention is not limited in its application to this specific form of adaptor and may be applied generally to other forms of device. In this respect, for example, the invention may be applied to various other connectors and valve devices that are used for coupling to catheters and other tubing in the medico-surgical field, and more especially, as illustrated in FIG. 8, to an alternative form of adaptor.

Referring to FIG. 8, the alternative form of adaptor 21 has a cup-shape body portion 22 with a tubular stem 23 that extends rearwardly from its base 24. The stem 23 is turned back on itself around its open end 27 to provide an external and circumferential claw 28 corresponding to the claw 8 on the stem 3 of the adaptor 1.

Manufacture of the adaptor 21 of FIG. 8 may be achieved in substantially the same manner as that of the adaptor 1 of FIGS. 1 to 3 using a method and tooling corresponding to those described above with reference to FIGS. 6 and 7.

I claim:

1. A tracheal-tube assembly, comprising a tracheal tube of resilient material having an open proximal end, a device retained in said proximal end of the tracheal tube for coupling the tube to a gas-circuit passageway having a diameter larger than that of said tracheal tube, said device having a substantially cylindrical body portion which has a base that is provided with a flared aperture, the diameter of said cylindrical body portion being dimensioned for close-fitting insertion into said gas-circuit passageway to establish said coupling, and said device having an open-ended tubular stem which is integral with and extends in one direction only away from the said base, the diameter of said tubular stem being less than that of said cylindrical body portion and said stem diameter being dimensioned for close-fitting insertion of said stem into said proximal end of the tracheal tube, one end of said tubular stem being located at and integral with said base and opening through said flared aperture in said base, the free end of said tubular stem being located within the tracheal tube in spaced relation to said base and having an integral tubular portion thereof which is turned back on itself to provide an external resilient claw at the free end of said stem for engaging with the inside of the resilient tracheal tube, the exterior of said tubular stem being smooth-surfaced and being tapered toward said free end thereof, said claw extending as a circumferential lip having a smoothly free edge disposed completely around said tubular stem between the opposing ends of said stem and within said proximal end of the tracheal tube, the resilient tracheal tube bearing up over the claw to hug the tubular stem tightly and resiliently between said claw and said base to provide a gas-tight seal therewith, and said resilient claw splaying outwardly from the tubular stem away from the said free end of said stem and being directed toward said base thereby to flexibly engage the interior surface of the tracheal tube for resisting withdrawal of the tracheal tube and stem from one another to maintain said tracheal tube and said device in assembled relation to one another when said cylindrical body portion of said device is inserted into and removed from said gas-circuit passageway.

* * * * *